May 8, 1973 W. H. JESSEL, JR., ET AL Plant Pat. 3,327
CHRYSANTHEMUM PLANT
Filed Sept. 3, 1971
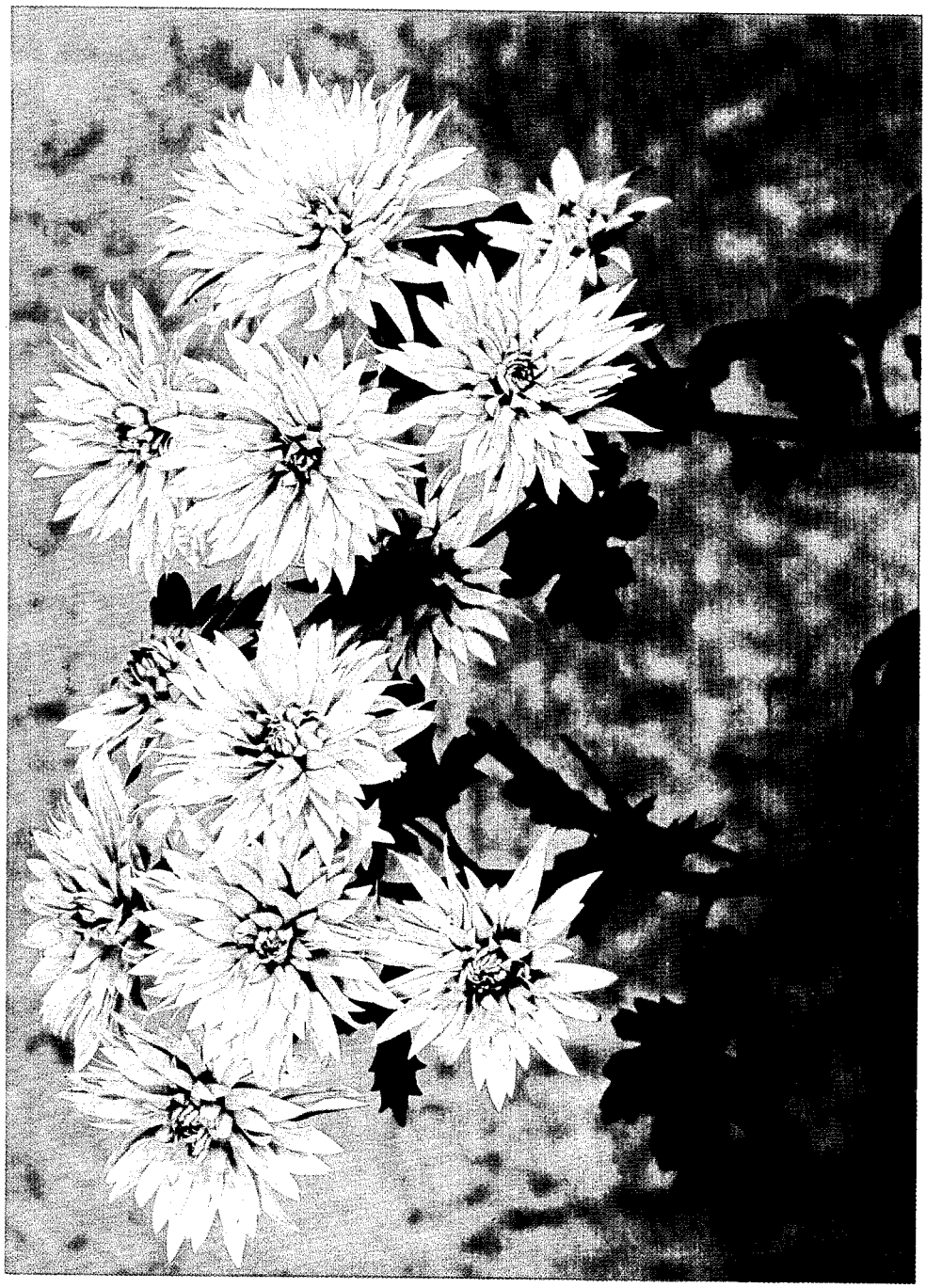

United States Patent Office

Plant Pat. 3,327
Patented May 8, 1973

3,327
CHRYSANTHEMUM PLANT

Walter H. Jessel, Jr., Doylestown, and William E. Duffett, Akron, Ohio, assignors to Yoder Brothers, Inc., Barberton, Ohio

Filed Sept. 3, 1971, Ser. No. 177,885
Int. Cl. A01h *5/00*
U.S. Cl. Plt.—79 1 Claim

The present invention comprises a new and distinct cultivar of chrysanthemum plant which is a sport of the cultivar known in the United States as Tally Ho, illustrated and described in our copending patent application Ser. No. 153,457, filed June 15, 1971.

The new cultivar is similar in many respects to Tally Ho, having the same characteristics of:

(1) Plant habit.
(2) Flowering response and period.
(3) Flower size and form.

The new cultivar is distinguished from Tally Ho by its light bronze flower color, when grown under comparable conditions.

weeks, and the following detailed description is based on observations made of the new cultivar in a greenhouse in Barberton, Ohio. The response time, blooming period, color, and total vigor may vary significantly with varying environmental conditions such as temperature, day length, and light intensity. Suggested flowering in the northern and western United States is from October through May; Florida, December through April.

The accompanying photographic drawing shows the unique characteristics of the new cultivar, the color being as nearly true as possible with color illustrations of this type. In the drawing, the new cultivar appears on the left and the parent cultivar Tally Ho on the right.

In the description which follows, color references are to the Munsell Color Book, 1963 edition, and comparisons are made with the cultivar Tally Ho. Where only a single value or description appears for the new cultivar, the same value or description applies to the parent cultivar as well.

Botanical classification: *Chrysanthemum morifolium*

| | Westward Ho | Tally Ho |
|---|---|---|
| Bloom: | | |
| Size | 2½–3¾ | |
| Fully expanded | 4¼" | |
| Borne | Clusters on elongated pedicels | |
| Stems | Wiry and strong | |
| Form | Decorative | |
| Permanence | 10–14 days | |
| Color: | | |
| Center of flower | Light yellow, 2.5Y8.5/6 | Light beige, 7.5YR8/4. |
| Base of petals | Yellow, 7.5Y8.5/8 | Pink, 2.5RP8/4. |
| Inside of petals | Bronze, 2.5YR5/8 to buff, 10YR9/1, streaking pink, 7.5R8/4 with extreme age. | Lavender pink, 2.5RP8/4. |
| Reverse of petals | Yellow bronze, 5YR8/4 to buff, 5YR9/1 | Lavender pink, 5RP8/4. |
| Tonality from a distance | Light bronze | Salmon pink. |
| Discoloration | Buff | Do. |
| Petals: | | |
| Texture | Smooth | |
| Appearance and form | Open at base, flat, broadens quickly; long and narrow terminating in a sharp point. | |
| Arrangement | Composite, whorled on a single receptacle | |
| Persistence | Resists shatter | |
| Fragrance | Typical chrysanthemum | |
| Reproductive organs: | | |
| Stamen, anthers | 0–5 | |
| Pollen | None | |
| Arrangement | Clustered in center of flower, if present | |
| Styles | Present both ray and disc florets | |
| Length | Short | |
| Ovaries | At the base of petal attached to receptacle | |
| Plant: | | |
| Form | Herbaceous | |
| Growth | Upright | |
| Height | Approximately 46" when grown as a single stem crop given 3–5 long day weeks and a total of 13–14 week crop time for the various seasons of the year as defined in the timetables published by Yoder Brothers, Inc. | |
| Spread | None when grown single stem to slight when pinched | |
| Foliage: | | |
| Top side | Dark green, 7.5GY4/4 | |
| Size | 6" long, 3½" wide | |
| Quantity | Numerous | |
| Shape | Spatulate lobed | |
| Texture | Coarse | |
| Ribs and veins | Prominent | |
| Edge | Deeply indented | |
| Serration | Coarse | |
| Under side | Light green, 5GY5/4 | |
| Stipules | Prominent base of stem, rudimentary upper portion | |

The new cultivar was selected from the flowering block of the parent cultivar at Barberton, Ohio, and when asexually reproduced by cuttings at Barberton, Ohio, has been found to retain its distinctive characteristics through successive propagations.

The new cultivar when grown in the vicinity of Barberton, Ohio, has a response period of approximately 10

We claim:

1. A new and distinct cultivar of chrysanthemum characterized particularly as to its uniqueness when compared to the parent cultivar Tally Ho by its light bronze color.

No references cited.

ROBERT E. BAGWILL, Primary Examiner